United States Patent [19]

Piercy

[11] 4,251,727
[45] Feb. 17, 1981

[54] GAS DETECTION

[76] Inventor: David R. Piercy, 6 Boswells Close, Bere Regis, Wareham, Dorset, England

[21] Appl. No.: 42,153

[22] Filed: May 24, 1979

[51] Int. Cl.$^2$ .......................................... G01N 21/26
[52] U.S. Cl. .................. 250/343; 356/437; 356/440
[58] Field of Search .............. 250/343, 344, 345, 373, 250/328; 356/51, 433, 436, 437, 440

[56] References Cited

U.S. PATENT DOCUMENTS

| | | | |
|---|---|---|---|
| 3,869,613 | 3/1975 | Link et al. | 250/343 |
| 3,904,880 | 9/1975 | Benz et al. | 250/343 |
| 3,950,101 | 4/1976 | Dewey, Jr. | 250/345 |
| 4,055,395 | 10/1977 | Honkawa et al. | 250/343 |

FOREIGN PATENT DOCUMENTS

| | | |
|---|---|---|
| 1181510 | 2/1970 | United Kingdom . |
| 1207243 | 9/1970 | United Kingdom . |
| 1352345 | 5/1974 | United Kingdom . |

Primary Examiner—Davis L. Willis

Attorney, Agent, or Firm—Birch, Stewart, Kolasch & Birch

[57] ABSTRACT

The invention provides an apparatus for detecting gases by absorption of infra-red radiation comprising a source of infra-red radiation arranged at one end of an optical path through the apparatus, at the other end of which path there is an infra-red detector. A plurality of cells located within an enclosure housing the cells are arranged to be moved in turn into the optical path in such position that when a cell is positioned on the optical path, the infra-red radiation passes through the cell before reaching the detector. The atmosphere to be tested is introduced into the enclosure and some of the cells are provided with means by which during movement of those cells through the enclosure into the optical path the atmosphere in the enclosure is pumped into the cell. Electronic means are provided for comparing the infra-red radiation received by the detector when one cell is positioned on the optical path with the infra-red radiation received by the detector when a different cell is positioned on the optical path and for producing a signal dependent on the comparison. The invention also provides a process for detecting gases using the apparatus of the invention.

7 Claims, 3 Drawing Figures

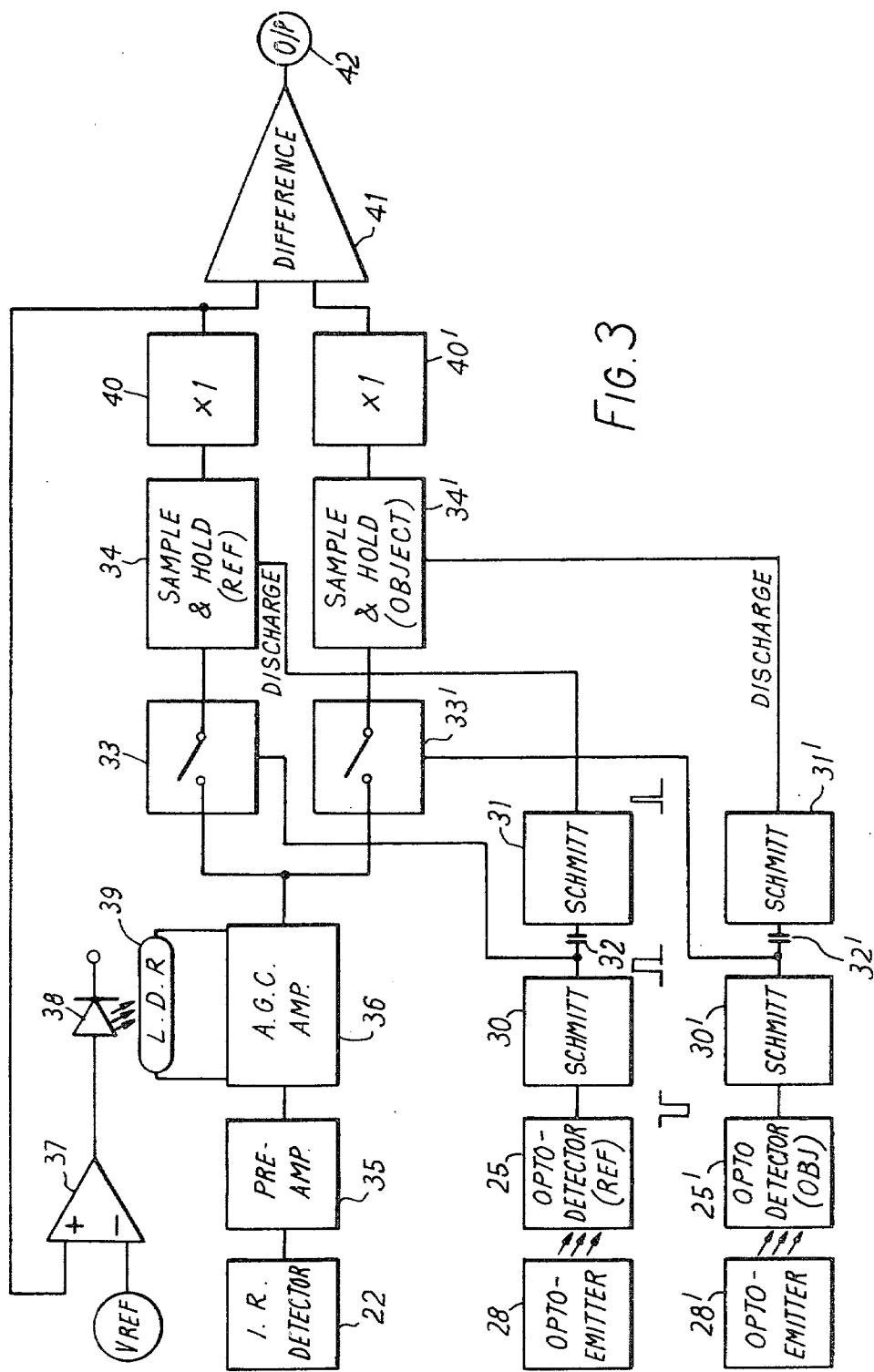

GAS DETECTION

BACKGROUND AND SUMMARY OF THE INVENTION

The present invention relates to the detection of gases using infra-red radiation.

In a known apparatus of this type, an emitter of infra-red radiation is situated at the focus of a mirror, which collimates the radiation and produces two beams that pass respectively through an object and a reference cell. The reference cell is sealed and contains usually dry air or nitrogen. The object cell is provided with two ports through which sample gas is pumped. The radiation emerging from the two cells is incident on a second mirror and is focussed on to an infra-red detector. A rotating chopper alternately allows energy from the reference and the object cell to reach the detector. A synchronizing device detects the position of the chopper and signals this position to controlling electronics, which process the pulses of information coming from the detector. The output of the system is determined according to the decrement in the energy of the beam which has passed through the object cell when compared to that emerging from the reference cell. If the object cell contains gas which absorbs infra-red radiation in the response band of the instrument, the radiation reaching the detector via the object cell will be reduced. The two alternate pulses of energy reaching the detector will therefore be of different magnitudes, and the processing electronics will output a D.C. voltage or current level which will be a measure of the decrement of energy transmitted through the object cell and hence a measure of the infra-red absorbing gas in the object cell. This technique is used extensively for the detection of many gases, notably hydrocarbons, which absorb radiation with wavelengths of approximately $3.4\mu$.

Disadvantages of this known type of apparatus are the need for focussing optical parts that can be upset by any movement of the apparatus and the relatively low proportion of the energy emitted by the infra-red emitter that is usefully employed. The energy dissipated heats the apparatus, so cooling is often necessary. Moreover, the time taken for the apparatus to reach a working condition from switch-on is relatively lengthy.

It is an object of the present invention to provide an apparatus in which these disadvantages are reduced.

According to the present invention there is provided apparatus for detecting gases by absorption of infra-red radiation comprising a source of infra-red radiation arranged at one end of an optical path of the apparatus at the other end of which is an infra-red detector, a plurality of cells arranged to be moved, in turn, into the optical path, the cells being such that when a cell is positioned on the optical path the infra-red radiation passes through that cell before reaching the detector, and electronic means for comparing the infra-red radiation received by the detector when one cell is positioned on the optical path with the infra-red radiation received by the detector when a selected other cell is positioned on the optical path and for producing a signal dependent on the said comparison.

Preferably, the cells are mounted for rotary motion about an axis parallel to the optical path of the apparatus and are moved successively into the optical path by said motion. Alternatively, the cells could be mounted as a pendulum or slide and moved in that way.

In the preferred form, the cells are housed within an enclosure and include one or more sealed reference cells containing e.g. nitrogen, dry air or a known concentration of a gas the detection of which is sought and an object cell that has openings in its side wall near its two ends whereby an atmosphere to be tested is pumped or allowed to pass into the enclosure and is pumped through the object cell by the motion of that cell through the enclosure.

In at least its preferred form, the present invention has the following advantages over the known apparatus.

All focussing optics are dispensed with, thus giving an improvement in stability and robustness.

A much greater portion of the energy emitted by the infra-red source is utilised, thus allowing a reduction in the power supplied to the source for an equivalent signal at the detector. A reduction to approximately one fifth of that supplied to a conventional source is easily possible, thus easing considerably the heat dissipation and warm-up problems associated with conventional equipment. A useful output can be obtained from the device in under two minutes from initial switch-on which compares very favorably with the warm-up time of many conventional instruments.

The self-pumping action of the object cell allows the device to be used as a direct monitor of the atmosphere of any particular area, since gas may be allowed to diffuse from such an area to the enclosure. Thus the external pump required in the conventional device is not required. Alternatively, the sample may be obtained from a distant area by using an external pump to draw the gas to be tested into the enclosure. Thus the installation of the device may be simplified and easily tailored to the particular application.

As mentioned above, there may be more than two cells. The additional cells could well be filled with samples of a variety of gases of interest, for example, methane, propane, butane, ethane, each at the alarm level(s) of interest. An external switch would allow the user to select whichever cell(s) are appropriate for the particular application. A synchronizing device forming part of the said electronic means then signals the processing electronics whenever the selected alarm level cell is at the optic axis, and thus gain and zero levels may be adjusted automatically by the electronics allowing the device to operate simply as a comparator, thus giving an extremely reliable alarm function.

If required, the single, static, infra-red filter may be replaced by a dual or multiple pass-band filter, thus allowing zero span and alarm adjustments to be made by the processing electronics from the detector outputs derived from a single cell. This would prevent cell window obscuration from causing errors due to outputs taken from different cells. The multiple infra-red filter system could be driven in synchronism by any suitable mechanical or electrical drive system.

BRIEF DESCRIPTION OF THE DRAWINGS

The invention will now be described, by way of example, with reference to the accompanying drawings, in which:

FIG. 3 is a block diagram of the electronic circuitry used in the apparatus shown in FIGS. 1 and 2.

DETAILED DESCRIPTION OF THE INVENTION

Figure 1:
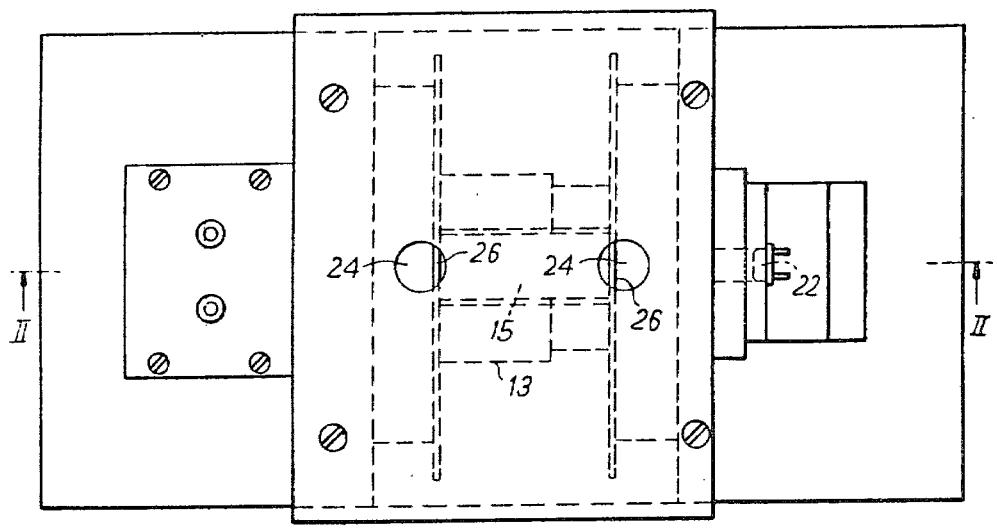
FIG. 1 is a plan view of an infra-red gas detection apparatus embodying the invention.
Figure 2:
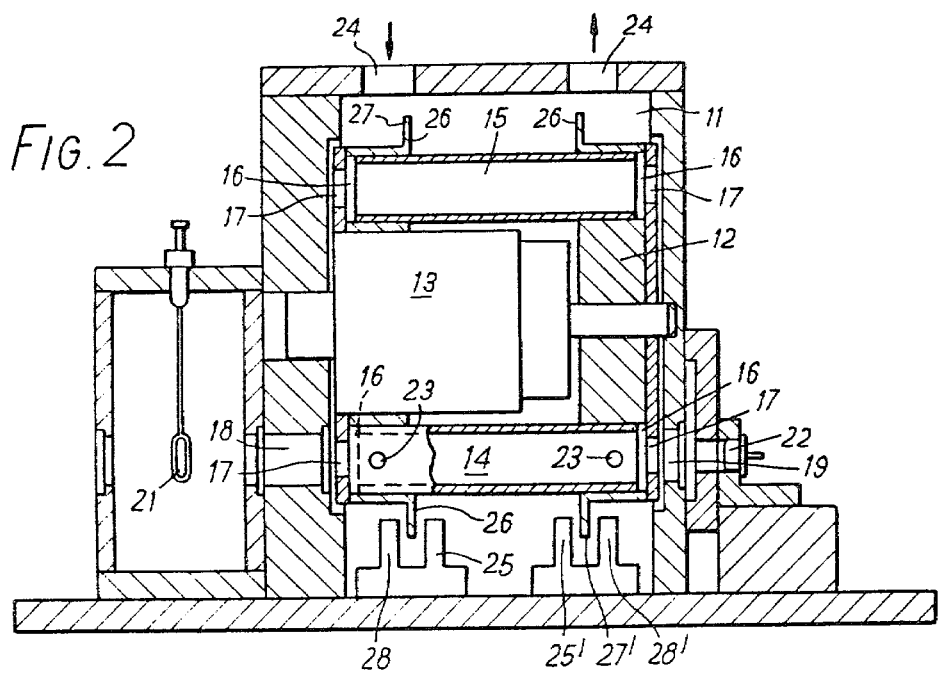
FIG. 2 is a sectional view on the line II—II in FIG. 1.

Referring firstly to FIGS. 1 and 2, the apparatus comprises an enclosure 11 within which is mounted, for rotation about a horizontal axis, a rotor 12 that is driven by a motor 13. The rotor 12 carries a cylindrical object cell 14 and a similar cylindrical reference cell 15. The cells 14 and 15 have infra-red transmitting end walls 16 in register with windows 17 on the end plates of the rotor, which end walls are so disposed that when each cell is at its lowermost position as seen in FIG. 2, its end walls 16 are in register with infra-red transmitting entry and exit windows 18 and 19 in the walls of the enclosure 11. The windows 18 and 19 lie on an optical path of the apparatus at one end of which, outside the enclosure, is a source 21 of infra-red radiation and at the other end of which, also outside the enclosure, is a detector 22 of infra-red radiation.

The reference cell 15 is sealed and contains nitrogen, or dry air. The object cell 14 has openings 23 in its sides positioned adjacent to its ends. As the cell 14 is moved through the enclosure, gas is pumped through it by means of the openings 23, so that the gas in the cell 14 is continually changed and is always effectively the same as that within the enclosure 11, which receives gas through the ports 24.

A pair of optical sensors 25 and 25' on the floor of the enclosure cooperate with light sources 28 and 28' and with notches 27 and 27' in flanges 26 and 26' of the cells respectively to detect which cell is, at any particular time, on the optical path of the apparatus. Notch 27 is adjacent the reference cell 15 in the left-hand flange 26 as seen in FIG. 2, and notch 27 is adjacent the object cell 14 in the right hand flange 26'.

FIG. 3 shows the electronic circuitry for providing an output for the apparatus. The two gas cells 14 and 15 passing the optical path allow two pulses of infra-red radiation to reach the detector 22 per rotation of the rotor 12. The two pulses outputted from the detector will, therefore, correspond to the signal obtained (1) via the object cell 14, and (2) via the reference cell 15. The optical synchronizing circuitry shown in FIG. 3 includes the sensors 25 and 25' the outputs of which are each applied to a respective Schmitt trigger circuit 30, 30'. A second schmitt trigger circuit 31, 31' is connected to the output of each of these first Schmitt circuits respectively via a capacitor 32, 32'. The output of each of the first Schmitt circuits is connected to the sampling switch 33, 33' of an appropriate sample and hold circuit 34, 34'. That is to say, switch 33 and circuit 34 together with a buffer amplifier 40 constitute sample-and-hold circuit for the reference signal and switch 33' and circuit 34' together with a buffer amplifier 40' constitute a sample-and-hold circuit for the object signal.

The output of detector 22 is pre-amplified in a pre-amplified 35 and then passed to a main automatic gain control (A.G.C.) amplifier 36. The notches 27 and 27' are so positioned as to ensure that triggering pulses from the Schmitt circuits 30, 30' close the appropriate switch 33, 33' when the corresponding cell is positioned in the optical path of the apparatus. In this way the reference and object signals are passed to two different halves of the circuit. The output of the sample and hold circuits 34, 34' are approximate D.C. voltage levels, which are "refreshed" once per rotation of the rotor. Before each new voltage pulse is passed from the detector, the appropriate holding capacitor is partially discharged by a "discharge" signal originating from the second Schmitt circuit 31, 31'. This allows the circuitry to rapidly follow falling voltage signals.

The voltage level from the reference sample and hold circuit 34 is fed back to be compared in a comparator 37 to a reference potential $V_{REF}$, and thence to a light emitting diode 38 which is coupled to a light dependent resistor 39, which adjusts the gain of the A.G.C. amplifier 36 to ensure that the reference output signal is maintained at a constant level, irrespective of changes in emitter or detector efficiency or cell window obscuration. Also, this voltage level is compared in a comparator 41 with the corresponding level from the object sample and hold circuit 34', the difference between the two levels constituting the output signal 42.

Since the object and reference signals are at all times subjected to the same amplification factors, and since the reference voltage is held at a constant level, the difference between the two signals is equivalent to a ratio signal, and thus is an accurate measure of the decrement in the infra-red radiation transmitted through the object cell compared with that transmitted through the reference cell. The output signal is, therefore, a measure of the infra-red absorbing gas present in the object cell.

I claim:

1. Apparatus for detecting gases by absorption of infra-red radiation comprising a source of infra-red radiation, and a detector for infra-red radiation, said source and said detector being arranged at opposite ends of an optical path through the apparatus, a plurality of cells including at least one sample cell and at least one reference cell arranged to be moved, in turn, into said optical path such as that when a cell is positioned in said optical path, infra-red radiation from said source passes through the cell before reaching said detector, and enclosure housing said cells and the part of said optical path into which said cells are arranged to be moved, means for introducing an atmosphere to be tested into said enclosure, means associated with at least one of said sampling cells by which during movement thereof through said enclosure into said optical path the atmosphere in the enclosure is pumped into said cell by the motion of said cell through the enclosure, and electronic means for comparing infra-red radiation received by the detector when said at least one sampling cell is positioned in said optical path with the infra-red radiation received by the detector when said at least one reference cell is positioned in said optical path, and means for producing a signal dependent on the said comparison.

2. Apparatus according to claim 1, wherein said cells are mounted for rotary motion about an axis parallel to said optical path of the apparatus and are moved successively into said optical path by said motion.

3. Apparatus according to claim 1, wherein said cells are mounted as a pendulum or slide for movement successively into said optical path.

4. Apparatus according to any of claims 1, 2 or 3, wherein said cells include at least one sealed reference cell and one or more sample cells, said sample cell having openings in its side wall at or near its ends whereby the atmosphere to be tested is pumped or allowed to pass through the cell through said openings by the motion of the cell through the enclosure.

5. Apparatus as claimed in claim 4 including a plurality of sealed reference cells each filled with a gas at a respective different alarm concentrations, and a selection switch to enable the sample cell or cells individually to be compared with any one or more of the reference cells.

6. A process for detecting gases by absorption of infra-red radiation which comprises moving, in turn, at least two of a plurality of cells including at least one sample cell and at least one reference cell into the optical path between a source of infra-red radiation and an infra-red detector so that infra-red radiation passes through the cell from said source to said detector, comparing the infra-red radiation received by said detector when one of said at least two cells is positioned in said optical path electronically with the infra-red radiation received by the detector when said at least one other cell is positioned in said optical path and producing a signal dependent on said comparison, said cell being housed in an enclosure into which an atmosphere to be tested is passed, said atmosphere being pumped into at least one of said at least two cells by the motion of said cell through said enclosure from a position outside said optical path to a position in said optical path.

7. A process as claimed in claim 6, wherein said cells comprise at least one sample cell through which said atmosphere is pumped and at least one sealed reference cell, and wherein said comparison is made between the infra-red radiation received by the detector when said at least one sample cell is positioned in said optical path with the radiation received by said detector when one of said at least one reference cell is positioned in said optical path.

* * * * *

REEXAMINATION CERTIFICATE (52nd)

United States Patent [19]

Piercy

[11] B1 4,251,727

[45] Certificate Issued Feb. 8, 1983

[54] GAS DETECTION

[75] Inventor: David R. Piercy, Wareham, England

[73] Assignee: J. & S. Sieger Limited, Poole, England

Reexamination Request
No. 90/000,136, Jan. 11, 1982

Reexamination Certificate for:
Patent No.: 4,251,727
Issued: Feb. 17, 1981
Appl. No.: 42,153
Filed: May 24, 1979

[51] Int. Cl. ................................................ G01N 21/26
[52] U.S. Cl. ........................ 250/343; 356/437; 356/440
[58] Field of Search ................ 250/343, 344, 345, 373, 250/328; 356/51, 433, 436, 437, 440

[56] References Cited

U.S. PATENT DOCUMENTS 3,987,303  10/1976  Stoft et al ............................ 250/343
4,075,481   2/1978  Stoft et al ............................ 250/343

*Primary Examiner*—Davis L. Willis

[57] ABSTRACT

The invention provides an apparatus for detecting gases by absorption of infra-red radiation comprising a source of infra-red radiation arranged at one end of an optical path through the apparatus, at the other end of which path there is an infra-red detector. A plurality of cells located within an enclosure housing the cells are arranged to be moved in turn into the optical path in such position that when a cell is positioned on the optical path, the infra-red radiation passes through the cell before reaching the detector. The atmosphere to be tested is introduced into the enclosure and some of the cells are provided with means by which during movement of those cells through the enclosure into the optical path the atmosphere in the enclosure is pumped into the cell. Electronic means are provided for comparing the infra-red radiation received by the detector when one cell is positioned on the optical path with the infra-red radiation received by the detector when a different cell is positioned on the optical path and for producing a signal dependent on the comparison. The invention also provides a process for detecting gases using the apparatus of the invention.

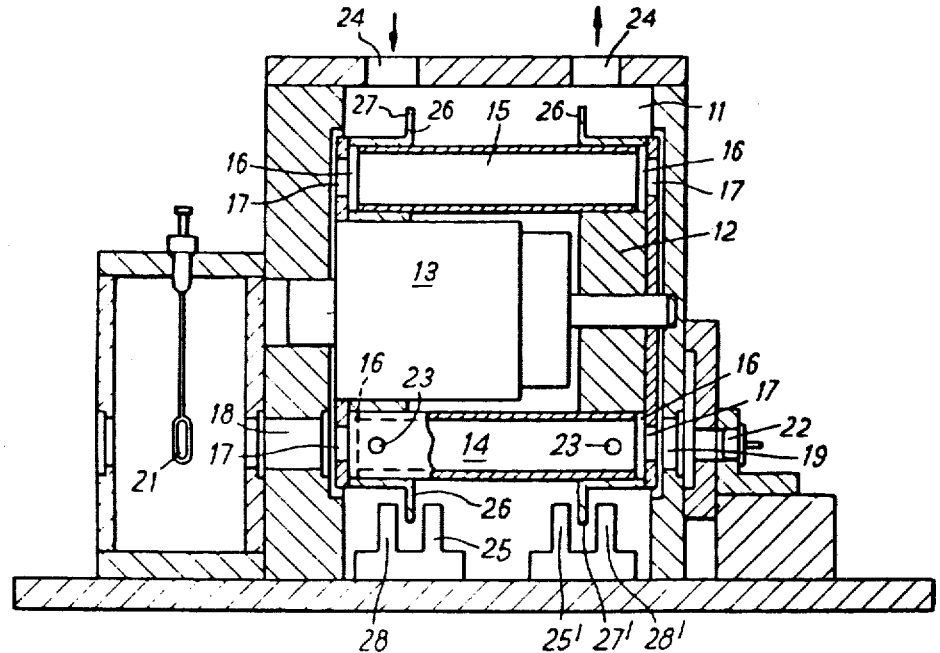

REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

AS A RESULT OF REEXAMINATION, IT HAS BEEN DETERMINED THAT:

Claims 1-5, having been finally determined to be unpatentable, are cancelled.

Claims 6 and 7 are determined to be patentable as amended.

6. A process for detecting *and continuously monitoring* gases by absorption of infra-red radiation which comprises *the following steps:*
moving, in turn, at least two of a plurality of cells including at least one *enclosed* sample cell and at least one reference cell into [the] *an* optical path between a source of infra-red radiation and an infra-red detector so that infra-red radiation passes through the cell from said source to said detector[.];
comparing the infra-red radiation received by said detector when one of said at least two cells is positioned in said optical path electronically with the infra-red radition received by the detector when said at least one other cell is positioned in said optical path and producing a signal dependent on said comparison[, said cell being housed];
*housing said cells in an enclosure into which an atmosphere to be tested is passed*[,];
*pumping* said atmosphere *through apertures in said enclosed sample cell facing generally along the path of movement of the sample cell* [being pumped into at least one of said at least two cells] by the motion of said *sample* cell through said enclosure from a position outside said optical path to a position in said optical path[.]. *said cells having a length extending substantially along the entire optical path from said source of infra-red radiation to said infra-red detector;*
*detecting and continuously monitoring said atmosphere pumped within said enclosed object sample cell.*

7. A process as claimed in claim 6, wherein said cells comprise at least one *enclosed* sample cell through which said atmosphere is pumped and at least one sealed reference cell, and wherein said comparison is made between the infra-red radiation received by the detector when said at least one *enclosed* sample cell is positioned in said optical path with the radiation received by said detector when one of said at least one reference cell is positioned in said optical path.

New claims 8-13 are added and determined to be patentable.

*8. An apparatus for detecting and continuously monitoring gases by absorption of infra-red radiation comprising:*
*a source of infra-red radiation arranged at one end of an optical path of the apparatus;*
*an infra-red detector arranged at the other end of said optical path;*
*a plurality of cells arranged to be moved, in turn, into the optical path, the cells being disposed so that when a cell is positioned on the optical path the infra-red radiation passes through that cell before reaching the detector; and*
*electronic means for comparing the infra-red radiation received by the detector when one cell is positioned on the optical path with the infra-red radiation received by the detector when a selected other cell is positioned on the optical path and for producing a signal dependent on the comparison;*
*said cells being housed within an enclosure and including one or more sealed reference cells having a length extending substantially along the entire optical path from said source of infra-red radiation to said infra-red detector, each containing a know concentration of a gas, and an enclosed object cell having a predetermined volume and extending substantially along the entire optical path from said source of infra-red radiation to said infra-red detector and including openings in a wall of said object cell facing generally along the path of movement of the cell whereby an atmosphere to be tested is pumped or allowed to pass into the enclosure and is pumped through the openings in said object cell by the motion of that cell through the enclosure to continuously monitor a changing atmosphere.*

*9. An apparatus according to claim 8, wherein the cells are mounted for rotary motion about an axis parallel to the optical path of the apparatus and are moved successively into the optical path by said motion.*

*10. An apparatus according to claim 8, wherein the cells are mounted as a pendulum or slide.*

*11. An apparatus according to claim 8, 9, or 10 wherein said object cell includes end portions and one of said openings being located in a side wall of the object cell near each of said end portions.*

*12. An apparatus according to claim 8, 9, or 10 and further including a plurality of sealed reference cells each filled with gas at a respective alarm concentration and a selector switch to enable the sample cells to be compared with any of the reference cells.*

*13. An apparatus according to claim 8, 9, or 10, wherein the electronic comparing means includes an automatic gain control amplifier connected to the output of the infra-red detector, and a control circuit arranged to compare an output derived from the automatic gain control amplifier when the reference cell is in the optical path, with a reference voltage and adjust the gain of the amplifier to hold the output to the reference voltage level.*

* * * * *